(12) United States Patent
Fanning et al.

(10) Patent No.: US 12,337,054 B2
(45) Date of Patent: Jun. 24, 2025

(54) SKIN TREATMENT COMPOSITION CONTAINING CANNABINOIDS

(71) Applicant: TF Holdings LLC, Aurora, CO (US)

(72) Inventors: Francis G. Fanning, Jackson, WY (US); Tobias C. Ripsom, Denver, CO (US); Marnie L. Peterson, Jackson, WY (US); William Onyebuagu, South Holland, IL (US)

(73) Assignee: TF Holdings LLC, Aurora, CO (US)

( * ) Notice: Subject to any disclaimer, the term of this patent is extended or adjusted under 35 U.S.C. 154(b) by 79 days.

(21) Appl. No.: 18/128,816

(22) Filed: Mar. 30, 2023

(65) Prior Publication Data

US 2023/0310297 A1    Oct. 5, 2023

Related U.S. Application Data

(60) Provisional application No. 63/326,626, filed on Apr. 1, 2022.

(51) Int. Cl.
*A61K 8/49* (2006.01)
*A61K 8/31* (2006.01)
*A61K 8/34* (2006.01)
*A61K 8/92* (2006.01)
*A61Q 17/00* (2006.01)
*A61Q 19/00* (2006.01)

(52) U.S. Cl.
CPC ............ *A61K 8/498* (2013.01); *A61K 8/31* (2013.01); *A61K 8/347* (2013.01); *A61K 8/922* (2013.01); *A61Q 17/005* (2013.01); *A61Q 19/00* (2013.01)

(58) Field of Classification Search
USPC ................................................ 514/454
See application file for complete search history.

(56) References Cited

U.S. PATENT DOCUMENTS

| | | |
|---|---|---|
| 10,441,552 B2 | 10/2019 | Anastassov et al. |
| 10,835,504 B2 | 11/2020 | Ganz et al. |
| 10,864,189 B2 | 12/2020 | Borok |
| 11,058,646 B2 | 7/2021 | Anastassov et al. |
| 2016/0120803 A1 | 5/2016 | Mathur et al. |
| 2019/0209487 A1 | 7/2019 | Anatassov et al. |
| 2019/0247299 A1 | 8/2019 | Cameron et al. |
| 2019/0321312 A1 | 10/2019 | Ganz et al. |
| 2020/0000765 A1 | 1/2020 | Borok |
| 2020/0016095 A1 | 1/2020 | Anastassov et al. |
| 2020/0345686 A1 | 11/2020 | Baillo et al. |
| 2020/0352849 A1 | 11/2020 | Rotunda |
| 2021/0046040 A1 | 2/2021 | Avram |
| 2021/0093690 A1 | 4/2021 | LaRosa et al. |
| 2021/0353699 A1 | 11/2021 | Afornali |
| 2021/0361590 A1* | 11/2021 | Lupia .......... A61K 31/593 |
| 2024/0041901 A1 | 2/2024 | Fanning et al. |
| 2024/0148762 A1 | 5/2024 | Fanning et al. |

FOREIGN PATENT DOCUMENTS

| | | | |
|---|---|---|---|
| CN | 103720610 A * | 4/2014 | |
| CN | 103841950 A * | 6/2014 | ............... A61K 8/37 |
| EP | 3 875 100 A1 | 9/2021 | |
| EP | 4268799 A1 | 11/2023 | |
| EP | 4316474 A1 | 2/2024 | |
| WO | 2014/126370 A1 | 8/2014 | |
| WO | 2016/133824 A1 | 8/2016 | |
| WO | 2021/224693 A1 | 11/2021 | |
| WO | 2021/236748 A1 | 11/2021 | |

OTHER PUBLICATIONS

Cowan et al., The Quantitation of Squalene and Squalane in Bronchoalveolar Lavage Fluid Using Gas Chromatography Mass Spectrometry, Frontiers in Chemistry, 2022, vol. 10, Article 874373, p. 1 (Year: 2022).*

Jackson et al., An Introduction to Hemp Chemistry and Lab Results, UGA Cooperative Extension Circular 1209, Jun. 2023, p. 5. (Year: 2023).*

Mahizan et al., Terpene Derivatives as a Potential Agent against Antimicrobial Resistance (AMR) Pathogens, Molecules, Jul. 19, 2019, vol. 24, No. 14, p. 2631 (Year: 2019).*

Alonso-Esteban et al., Fatty acids and minor functional compounds of hemp (*Cannabis sativa* L.) seeds and other *Cannabaceae* species, Journal of Food Composition and Analysis, 2023, vol. 115, article 104962, p. 7. (Year: 2023).*

Parker et al., Moisturisers for the treatment of foot xerosis: a systematic review, Journal of Foot and Ankle Research, Feb. 2017, vol. 10(9), p. 1. (Year: 2017).*

CN-103720610-A (WIPO English Translation of Description, Downloaded Sep. 2024) (Year: 2024).*

CN-103720610-A (WIPO English Translation of Claims, Downloaded Sep. 2024) (Year: 2024).*

CN-103841950-A (WIPO English Translation of Description, Downloaded Sep. 2024) (Year: 2024).*

"Cellular Recovery Complex," Record ID 1118009 from MINTEL, Jun. 2009, pp. 8. (XP093102086).

"Intensive Nourishing Night Cream with Ceramides," Record ID 9794186 from MINTEL, Aug. 2022, pp. 5. (XP93102084).

(Continued)

*Primary Examiner* — Jeffrey H Murray
*Assistant Examiner* — Rilla Marie Samsell
(74) *Attorney, Agent, or Firm* — Kagan Binder PLLC (57) ABSTRACT

A skin care product comprising one or more cannabinoids and one or more triglyceride oils is disclosed. The cannabinoids used in the product may be CBD, THC, or a mixture thereof. The triglyceride oil used in the product may be squalene, meadowfoam seed oil, or a mixture thereof. The cannabinoid and triglyceride compounds may be naturally derived products. The skin care product exhibits beneficial anti-microbial and/or skin rejuvenating properties and may be used to treat a human or an animal. Some skin disorders that may be treated with the product include acne, xerosis and wrinkled skin.

14 Claims, 9 Drawing Sheets

(56) References Cited

OTHER PUBLICATIONS

"Universal Skincare Outer Space Renewal Oil," Record ID 8574233 from MINTEL, Mar. 2021, pp. 11. (XP093075098).
Weigelt et al., "The therapeutic potential of cannabinoids for integumentary wound management," Experimental Dermatology, vol. 30, No. 2, Nov. 2020, pp. 201-211.
Extended European Search Report pursuant to Rule 62 EPC, from counterpart European Application No. 23189109.4, dated Dec. 12, 2023, 10 pp.
"Body Balm," Record ID 6985487 from MINTEL, Nov. 2019, pp. 7. (XP093075095).
Li et al., "Identification of COL1A1 and COL1A2 as candidate prognostic factors in gastric cancer," World of Journal of Surgical Oncology, vol. 14, No. 1, Nov. 2016, Article No. 297 (pp. 5).
Paramasivan et al., "Recent advances in the microbial production of squalene," World Journal of Microbiology and Biotechnology, vol. 38, No. 5, Apr. 2022, Article No. 91, pp. 21.
Popa et al., "Methods for Obtaining and Determination of Squalene from Natural Sources," BioMed Research International, vol. 2015, Article No. 356292, Jan. 2015, (pp. 17).
Sholler et al., "Therapeutic potential and safety considerations for the clinical use of synthetic cannabinoids," Pharmacology Biochemistry and Behavior, vol. 199, Oct. 2020, Article No. 173059, (pp. 38).
Song et al., "Production of Squalene in Bacillus subtilis by Squalene Synthase Screening and Metabolic Engineering," Journal of Agricultural and Food Chemistry, No. 68, No. 15, Mar. 2020, pp. 4447-4455.
Extended European Search Report pursuant to Rule 62 EPC, from counterpart European Application No. 23165774.3, dated Sep. 28, 2023, 9 pp.
U.S. Appl. No. 18/228,881, filed Aug. 1, 2023, naming inventors Fanning et al.
U.S. Appl. No. 18/388,057, filed Nov. 8, 2023, naming inventors Fanning et al.
"Emerald *Cannabis sativa* (Hemp) Deep Moisture Glow Oil," Record ID 6401959 from MINTEL, Mar. 2019, pp. 8. (XP093064787).
Extended European Search Report pursuant to Rule 62 EPC, from counterpart European Application No. 23208680.1, dated Jun. 17, 2024, 9 pp.

\* cited by examiner

SKIN TREATMENT COMPOSITION CONTAINING CANNABINOIDS

This application claims the benefit of U.S. Provisional Patent Application No. 63/326,626, filed Apr. 1, 2022, the disclosure of which is incorporated in its entirety herein by reference.

BACKGROUND

Your skin is the body's largest organ and covers and protects your body. The purposes of the skin are vast: it holds body fluids in; prevents dehydration; keeps harmful microbes out; prevents infections; helps you feel things like heat, cold and pain; keeps your body temperature; and makes vitamin D when the sun shines on it. Anything that irritates, clogs or inflames your skin can cause symptoms such as redness, swelling, burning, and itching. Allergies, bacteria, viruses, irritants, genetic makeup, and certain diseases and immune system problems, can cause rashes, hives and other skin conditions.

There are many different types of skin disorders and they vary greatly in symptoms and severity. They can be temporary or permanent, and may be painless or painful. Some have situational causes, while others may be genetic. Some skin conditions are minor and others can be life-threatening. Some common skin disorders include acne vulgaris (acne), atopic dermatitis (eczema), herpes zoster (shingles), urticaria (hives), sunburn, cold sores, dry skin, psoriasis, vitiligo, contact dermatitis, rosacea, melasma, diaper rash, warts and actinic keratosis. The pharmaceutical and cosmetic industries have brought many products to market to address a plethora of skin disorders, with a prevalence to cleaning the skin, perfuming it, changing its appearance, correcting body odours, and protecting or keeping it in good condition.

Cannabinoids are the subject of much research in the pharmaceutical and cosmetic industries. Patents and patent applications in this field include U.S. Pat. Nos. 10,441,552; 10,835,504; 10,864,189; 11,058,646; US 2016/0120803; US 2020/0352849; US 2021/0046040; and EP 3 875 100. These and other publications disclose the use of cannabinoids in compositions to treat various skin disorders, such as, toe nail fungus, MRSA infection, herpes virus infection, tinea pedis, burn and other wound infections, sun burn, diabetic infection, eczema, impetigo, dermatophytosis, psoriasis, itchy skin, painful skin, inflamed skin, atopic dermatitis, dandruff, pruritus ani, and general topical infections. These and other cannabinoid-containing compositions provide treatments for many skin disorders. However, many of these types of compositions and methods suffer from significant limitations and do not treat all types of skin disorders.

Thus, there exists a need for new cannabinoid-containing compositions and methods to use these compositions to better treat skin disorders.

The approach described in this disclosure seeks to meet this need by providing novel cannabinoid-containing compositions and methods to treat a variety of skin disorders.

SUMMARY

This disclosure provided a topical anti-microbial composition for use on skin comprising the combination of a pharmacologically effective amount of one or more cannabinoids and a one or more triglyceride oils in a suitable base.

In an embodiment, the composition comprises:
(i) about 0.05-5.00% by weight of at least one cannabinoid; and
(ii) about 1.00-42.00% by weight of at least one triglyceride oil.

In other embodiments:
(a) the cannabinoid and the triglyceride oil each comprise a naturally derived product;
(b) the cannabinoid comprises CBD, THC, or CBD and THC (as defined below);
(c) the CBD comprises about 0.25-1.10% by weight of the total composition;
(d) the composition comprises about 0.25-1.10% by weight of CBD and about 0.25-1.50% by weight of THC;
(e) the triglyceride oil comprises meadowfoam seed oil, squalene, or meadowfoam seed oil and squalene;
(f) the composition comprises about 5.00-20.00% by weight of meadowfoam seed oil and about 4.00-15.00% by weight of squalene; and/or
(g) the composition comprises about 0.25-1.10% by weight of CBD, about 0.25-1.50% by weight of THC, about 5.00-20.00% by weight of meadowfoam seed oil, and about 4.00-15.00% by weight of squalene.

In another embodiment, the composition base comprises one or more of the following ingredients: a solvent, a thickener, an anti-oxidant, a conditioner, a moisturizer, an emulsifier, a nutrient, an aroma, a preservative, a stabilizer, or a combination thereof.

The disclosure also provides a method for treating skin disorders by applying a therapeutically effective amount of the composition to the skin of a human or an animal in need of treatment.

The anti-microbial compositions and methods of use described herein are helpful for treating a variety of skin disorders, particularly, acne and other microbial skin conditions.

The foregoing and other objects and features of the disclosure will become more apparent from the following detailed description, which proceeds with reference to the accompanying figures. Further embodiments, forms, features, aspects, benefits, objects and advantages of the disclosure shall become apparent from the detailed description and figures provided herewith.

While the present disclosure is susceptible to various modifications and alternative forms, exemplary embodiments thereof are shown by way of example in the drawings and are herein described in detail. It should be understood, however, that the description of exemplary embodiments is not intended to limit the disclosure to the particular forms disclosed, but on the contrary, the intention is to cover all modifications, equivalents and alternatives falling within the spirit and scope of the disclosure as defined by the embodiments herein and the claims below. Reference should therefore be made to the embodiments and claims for interpreting the scope of the disclosure.

DETAILED DESCRIPTION

New composition comprising a cannabinoid and a triglyceride oil to treat skin disorders are described Below are definitions for some of the terms used in this disclosure.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrase "one or more" is readily understood by one of skill in the art, particularly when read in context of its usage. For example, the phrase can mean one, two, three, four, five, six, ten, 100, or any upper limit approximately 10, 100, or 1000 times higher than a recited lower limit.

As will be understood by the skilled artisan, all numbers, including those expressing quantities, properties, purities, reaction conditions, and so forth, are approximations and are understood as being optionally modified in all instances by the term "about." These values can vary depending upon the desired goals sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by the skilled artisan, all numbers, including those expressing quantities, properties, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language, such as "up to", "at least", "greater than", "less than", "more than", "or more", and the like, include the number recited, and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the disclosure encompasses not only the entire group listed as a whole, but each member of the group individually and all possible subgroups of the main group. Additionally, for all purposes, the disclosure encompasses not only the main group, but also the main group absent one or more of the group members. The disclosure therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., on the skin of a human or animal, in a solution, in a reaction mixture, in vitro, or in vivo.

An "effective amount" refers to an amount effective to bring about a recited effect, such as an amount necessary to form a product(s) in a reaction mixture. Determination of an effective amount is typically within the capacity of persons skilled in the art, especially in light of the detailed disclosure provided herein. The term "effective amount" is intended to include an amount of a compound described herein, or an amount of a combination of compounds described herein, e.g., that is effective to form a product(s) in a reaction mixture. Thus, an "effective amount" generally means an amount that provides the desired effect.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

The terms "cannabinoid" and "cannabinoids" include, but are not limited to, natural phytocannabinoids, organic cannabinoids, endocannabinoids, cannabinoid analogs, cannabinoid derivatives, synthetic cannabinoids and cannabinoid receptor agonists. "Cannabinoid" means any compound that interacts with a cannabinoid receptor and other cannabinoid mimetics, including, but not limited to, certain tetrahydropyran analogs (delta-9-tetrahydrocannabinol, delta-8-tetrahydrocannabinol, 6,6,9-trimethyl-3-pentyl-6H-dibenzo[b,d]pyran-1-ol, 3-(1,1-dimethylheptyl)-6,6a7,8,10, 10a-hexahydro-1-1hydroxy-6,6-dimethyl-9-H-dibenzo[b,d] pyran-9-ol,(−)-(3 S,4S)-7-hydroxy-delta-6-tetrahydrocannabinol-1,1-dimethylheptyl, (+)-(3 S,4S)-7-hydroxy-A-6-tetrahydrocannabinol, and delta-8-tetrahydrocannabinol-11-oic acid); certain piperidine analogs (e.g., (−)-(6S,6aR,9R,10aR)-5,6,6a,7,8,9,10,10a-octahydro-6-methyl-1-3-[(R)-1-m-ethyl-4-phenylbutoxy]-1,9-phenanthridinediol 1-acetate)); certain aminoalkylindole analogs (e.g., (R)-(+)-[2,3-dihydro-5-methyl-3-(4-morpholinylm-ethyl)-pyrrolo[1,2,3,-de-]-1,4-benzoxazin-6-yl]-1-naphthelenyl-methanone); certain open pyran-ring analogs (e.g., 2-[3-methyl-6-(1-methylethenyl-2-cyclohexen-1-yl]-5-pentyl-1,3-benzendi-o-1, and 4-(1,1-dimethylheptyl)-2,3'-dihydroxy-6'-a-(3-hydroxypropyl)-1',-2'-,3',4',5',6'-hexahydrobiphenyl), their salts, solvates, metabolites, and metabolic precursors.

The term "cannabidiol" refers to cannabidiol and cannabidiol derivatives. As used herein, cannabidiol can be obtained from plant extract, for example hemp, with a trace amount of delta-9-tetrahydrocannabinol or from Cannabis extract using a high-cannabidiol Cannabis cultivar.

The following abbreviations will be used herein for two cannabinoids: "CBD" for cannabidiol; and "THC" for delta-9-tetrahydrocannabinol.

The art of formulating a skin care composition to treat skin disorders entails the sophisticated application of multiple scientific disciplines, e.g., chemistry, biology, physics, mathematics and materials. One of the common challenges to a formulator is how best to mix an active ingredient(s) with other ingredients (inactive or other active ingredients) to improve the efficacy of the composition. Experimentation illustrates the use of a naturally derived cannabinoid(s) (active ingredient) in a skin treatment formulation can be enhanced by combining it with a triglyceride oil, particularly, with a naturally derived triglyceride oil(s), such as meadowfoam seed oil and/or squalene. The use of a naturally derived cannabinoid(s), such as CBD, THC, or a combination of CBD and THC, together with a naturally derived triglyceride oil, such as meadowfoam seed oil and/or squalene, provides a beneficial skin care formulation for the treatment of a variety of skin disorders.

Cannabinoids are terpenophenolic compounds found in the Cannabis plant belonging to the Cannabaceae family. Cannabinoids can be isolated, for example, by extraction processes or cold pressing from Cannabis plants. Plants in the Cannabis genus include Cannabis sativa, Cannabis ruderalis, and Cannabis indica. These plants are the natural sources of cannabinoids, a preferred embodiment of the disclosure. Cannabinoids are also available in synthetic forms.

Examples of cannabinoids, cannabinoid analogs and cannabinoid derivatives include, but are not limited to, cannabigerolic acid (CBGA), cannabigerolic acid monomethylether (CBGAM), cannabigerol (CBG), cannabigerol monomethylether (CBGM), cannabigerovarinic acid (CBGVA), cannabigerovarin (CBGV), cannabichromenic acid (CBCA), cannabichromene (CBC), cannabichromevarinic acid (CBCVA), cannabichromevarin (CBCV), cannabidiolic acid (CBDA), cannabidiol (CBD), cannabidiol monomethylether (CBDM), cannabidiol-$C_4$ (CBD-$C_4$), cannabidivarinic acid (CBDVA), cannabidivarin (CBDV), cannabidiorcol (CBD-$C_1$), delta-9-tetrahydrocannabinolic acid A (THCA-A), delta-9-tetrahydrocannabinolic acid B (THCA-B), delta-9-tetrahydrocannabinol (THC), delta-9-tetrahydrocannabinolic acid-$C_4$ (THCA-$C_4$), delta-9-tetrahydrocannabinol-$C_4$ (THC-$C_4$), delta-9-tetrahydrocannabivarinic acid (THCVA), delta-9-tetrahydrocannabivarin (THCV), delta-9-tetrahydrocannabiorcolic acid (THCA-$C_1$), delta-9-tetrahydrocannabiorcol (THC-$C_1$), delta-7-cis-iso-tetrahydrocannabivarin, delta-8-tetrahydrocannabinolic acid ($\Delta^8$-THCA), delta-8-tetrahydrocannabinol ($\Delta^8$-THC), cannabicyclolic acid (CBLA), cannabicyclol (CBL), cannabicyclovarin (CBLV), cannnabielsoic acid A (CBEA-A), cannabielsoic acid B (CBEA-B), cannabielsoin (CBE), cannabinolic acid (CBNA), cannabinol (CBN), cannabinol methylether (CBNM), cannabinol-$C_4$ (CBN-$C_4$), cannabivarin (CBV), cannabinol-$C_2$ (CBN-$C_2$), cannabiorcol (CBN-$C_1$), cannabinodiol (CBND), cannabinodivarin (CBVD), cannabitriol (CBT), 10-ethoxy-9-hydroxy-delta-6a-tetrahydrocannabinol, 8,9-dihydroxy-delta-6a-tetrahydrocannabinol, cannabitriolvarin (CBTV), ethoxy-cannabitriolvarin (CB TVE), dehydrocannabifuran (DCBF), cannabifuran (CBF), cannabichromanon (CBCN), cannabicitran (CBT), 10-oxo-delta-6a-tetrahydrocannabinol (OTHC), delta-9-cis-tetrahydrocannabinol (cis-THC), 3,4,5,6-tetrahydro-7-hydroxy-alpha-alpha-2-trimethyl-9-n-propyl-2,6-metha-no-2H-1-benzoxocin-5-methanol (OH-iso-HHCV), cannabiripsol (CBR) and trihydroxy-delta-9-tetrahydrocannabinol (triOH-THC).

In a particular embodiment of the disclosure, the cannabinoid is a naturally derived product. Naturally derived cannabinoids can be found in a Cannabis sativa plant variety. Both CBD and THC are commercially available in large quantities. The art has shown that there are cannabinoid receptor sites in the human central nervous system and other tissues, and have labelled two of these sites as "CB1" and "CB2". These receptor sites, and their endogenous ligands, comprise the endocannabinoid system. CB1 receptors have also been found in other mammalian tissue, such as in the heart, lung, pituitary glands, etc. CB2 receptor sites can be found in immune cells. The combination of CB1 and CB2 receptors can play an important role in regulating the release of 'messages' to our body, i.e., CB1 receptors from neurons and CB2 receptors from immune cells.

Cannabinoids are usually characterized by low solubility in water and high solubility in lipid mixtures. They do not easily adhere to or remain on skin, and have limited penetration properties. Given these limitations, it is challenging for a skin care formulator to find the best (inactive) co-ingredients, and the best loading requirements, to enhance the efficacy of a cannabinoid (active ingredient) in the composition when it is applied to and comes in contact with the skin of a human or an animal.

Naturally derived oils have been studied and marketed for a variety of skin disorders by both the pharmaceutical and cosmetic industries. Some examples include coconut, almond, grapeseed, olive, sunflower seed, argan, rosehip see, jojoba, marula, tea tree and safflower oils. Similarly, "essential oils" have also been the subject of much study in the skin care field. Examples of essential oils include lavender, chamomile, sandalwood, clary sage, rosemary, frankincense, geranium, neroli, lemon, lemongrass, cinnamon, tea tree, peppermint, wintergreen, eucalyptus, patchouli, pomegranate, carrot seed, tangerine, ylang, rose, myrrh and jojoba oils. Though essential oils and naturally derived oils are both based on plants, there are clear differences between the two classes.

Essential oils are distilled from the leaves, roots, bark and other aromatic portions of a plant/botanical. These oils evaporate and have a concentrated aroma. Essential oils are concentrated, hydrophobic liquids containing volatile aroma compounds from plants. Essential oils are almost always diluted with a carrier oil because they are so potent and can cause irritation to the skin.

In contrast, fixed naturally derived oils are usually pressed from the fatty portions of a plant or botanical, such as the seeds, nuts or kernels. Naturally derived oils are triglycerides in which the glycerin is esterified with three fatty acids. They are the main constituent of vegetable oil and animal fats. Natural oils are generally gentle on the skin and do not require a carrier oil.

We have determined that the efficacy of a naturally derived cannabinoid in a skin care composition can be enhanced by formulating it with a naturally derived triglyceride oil. In one aspect of the disclosure, skin care properties of naturally derived cannabinoids, such as CBD and/or THC, can be enhanced by combining them with a naturally derived triglyceride oil, such as meadowfoam seed oil and/or squalene. The triglyceride oil can serve as an emollient, a penetration enhancer and/or a dispersion agent of the cannabinoid.

Naturally derived hydrogenated squalene is highly stable to oxidation. It can be found in olives and other vegetable-derived substances, such as wheat germ. Due to its stability, emollience, and moisturizing effects, squalene can play a valuable role in maintaining the skin barrier film, thereby preventing trans epidermal moisture loss.

Naturally derived meadowfoam seed oil is a high molecular weight fatty acid oil, which can be expressed from the seeds of the Meadowfoam plant (*Limnanthes alba*). This plant is widely cultivated as a cash crop in the State of Oregon and selected geographic areas of Canada. A typical fatty acid profile is: eicosenoic acid C20: 1-61%; docosenoic acid C22: 1-16%; and docosadienoic acid C22: 2-18%. Medowfoam seed oil typically contains some phytosterols. One of its properties is that it is a liquid at relatively low and ambient (i.e., room) temperatures and stable at both high and very low (i.e., freezing) temperatures. In addition, it readily absorbs into the epidermal region of the skin. As a carrier oil, meadowfoam seed oil is non-comedogenic and does not clog skin pores. It can perform as an emollient and skin softener in a skin care composition. It is commonly used in skin care products to help balance sebum production. It can also serve as a 'carrier' for an active ingredient into the epidermal region of the skin.

Most commonly used triglyceride oils are synthetic. Several skin care products contain caprylic capric triglycerides. While it is technically made of natural components, the caprylic triglyceride used in most products is usually not found in nature. Rather, a chemical process is performed to separate the oily liquid and produce a 'purer' version of it so that it can be added to the products.

In distinction, squalene and meadowfoam seed oil are high molecular weight, stable naturally derived (plant) oils that can enhance the penetration of a composition to the outer level of the skin. Exemplified embodiments show that a combination of squalene and meadowfoam seed oil serve as a delivery base for CBD and/or THC. (See Examples 1-3). In some embodiments these two naturally derived triglyceride oils 'surround' or 'encase' the molecules of the CBD and the THC, thereby holding them 'intact' or 'stable' until they are released onto the skin. Both of the oils can also function to help penetration of the composition to the epidermal region of the skin, thereby delivering enhanced efficacy to the lower levels of the skin.

One aspect of the disclosure is to utilize only naturally derived (as opposed to synthetic) oils in the skin care compositions. Ingredients used in the cosmetic industry are given a chemical name by "INCI"—International Nomenclature Cosmetic Ingredient. Even though one ingredient might have a similar name to another ingredient, two naturally derived ingredients might not be exactly the same. Thus, any 'substitute' ingredient for squalene and meadfoam seed oil can only be suggested after extensive testing in the formulation, including stability and human comparative focus studies.

The disclosure addresses some of the limitations in skin care products by developing a new composition comprising naturally derived cannabinoid(s) and naturally derived oil (s). This disclosure provides a new anti-microbial, anti-bacterial and anti-acne composition for use on skin comprising the combination of a cannabinoid and a triglyceride oil. One aspect of the disclosure is a formulation having (i) about 0.05-5.00% by weight of at least one cannabinoid and (ii) about 1.00-42.00% by weight of at least one triglyceride oil. The cannabinoid and the triglyceride oil each can comprise a natural product. Exemplary cannabinoids include CBD, THC, or CBD and THC. In one embodiment, the CBD comprises about 0.25-1.10% by weight of the total composition. In another embodiment, the composition comprises about 0.25-1.10% by weight of CBD and about 0.25-1.50% by weight of THC.

In particular embodiments, the triglyceride oil comprises meadowfoam seed oil, squalene, or meadowfoam seed oil and squalene. In one formulation, the composition comprises about 5.00-20.00% by weight of meadowfoam seed oil and about 4.00-15.00% by weight of squalene. In another formulation, the composition comprises about 0.25-1.10% by weight of CBD, about 0.25-1.50% by weight of THC, about 5.00-20.00% by weight of meadowfoam seed oil, and about 4.00-15.00% by weight of squalene.

In other embodiments, the composition further comprises one or more of the following ingredients: a solvent, a thickener, an anti-oxidant, a conditioner, a moisturizer, an emulsifier, a nutrient, an aroma, a preservative, a stabilizer, or a combination thereof.

We further describe herein a method for treating skin disorders by applying the novel compositions described therein to the skin of a human or an animal in need of treatment. When the composition comes in contact with the skin, the cannabinoid ingredient (active ingredient) can treat or ameliorate a variety of skin disorders.

The anti-microbial compositions and methods of use described herein are helpful for treating a variety of skin disorders, particularly, acne and other microbial skin conditions.

In embodiments, a topical composition of the disclosure may further comprise an inactive ingredient, such as a solvent, stabilizer, thickener, anti-oxidant, conditioner, moisturizer, preservative, nutrient, fragrance, cationic, ionic and non-ionic surfactant, antipruritic agent, antiperspirant, antipsoriatic agent, antiseborrheic agent, anti-aging agent, anti-wrinkle agent, skin lightening agent, depigmenting agent or vitamin.

The composition may also further comprise one or more active ingredients, such as an antibiotic, an antiseptic agent, an antifungal, an antibacterial agent, an analgesic an anti-viral agent, an anesthetic, an anti-cancer agent or an anti-acne agent.

In embodiments, a topical composition can be in the form of an ointment, a cream, an emulsion, a lotion, a paste, an unguent, a gel or a sunscreen. In a particular embodiment, the formulation is a cream, for example, a cream that would be applied at night while at home and without any other composition being applied to the skin. Creams according to the disclosure include water-in-oil or oil-in-water emulsions and may further comprise a cleansing agent, an emollient or an aromatic chemical compound. Ointments and unguents according to the disclosure optionally contain oil and water that can be in a ratio from about 2:1 to 7:1, and may further comprise a wax, alcohol or petroleum-based mollifying agents.

Gels according to the disclosure optionally contain a vegetable oil up to 5% by weight of the total composition, water and a thickening agent. The thickening agent may be a natural polysaccharide, such as xanthan gum, carrageen, alginate or cellulose gum.

Pastes according to the disclosure may optionally contain aloe gel and beeswax.

Lotions according to the disclosure include oil-in-water or water-in-oil emulsions and may comprise cetyl alcohol, an emulsifier, a fragrance, glycerol, petroleum jelly, a dye, one or more preservatives and/or a stabilizing agent.

A sunscreen composition according to the disclosure may further comprise a UV absorbing or barrier agent in an amount of between about 0.1 and 10% by weight of the composition. Exemplary UV-absorbing compounds include, but are not limited to, benzoic compounds, glyceryl PABA, roxadimate, octocrylene, octyl methoxycinnamate, ethoxyethyl p-methoxycinnamate, homomenthyl salicylate, ethylhexyl salicylate, trolamine salicylate, ecamsule, ensulizole, bemotrizinol and bisoctrizole. Exemplary UV-barrier compounds include but are not limited to, zinc oxide and titanium dioxide.

Exemplary antibiotics include, but are not limited to, ampicillin, bacampicillin, carbenicillin indanyl, mezlocillin, piperacillin, ticarcillin, amoxicillin-clavulanic acid, ampicillin-sulbactam, benzylpenicillin, cloxacillin, dicloxacillin, methicillin, oxacillin, penicillin G, penicillin V, piperacillin tazobactam, ticarcillin clavulanic acid, nafcillin, procaine penicillin, cefadroxil, cefazolin, cephalexin, cephalothin, cephapirin, cephradine, cefaclor, cefamandol, cefonicid, cefotetan, cefoxitin, cefprozil, ceftmetazole, cefuroxime, loracarbef cefdinir, ceftibuten, cefoperazone, cefixime, cefotaxime, cefpodoxime proxetil, ceftazidime, ceftizoxime, ceftriaxone, cefepime, azithromycin, clarithromycin, clindamycin, dirithromycin, erythromycin, lincomycin, troleandomycin, cinoxacin, ciprofloxacin, enoxacin, gatifloxacin, grepafloxacin, levofloxacin, lomefloxacin, moxifloxacin, nalidixic acid, norfloxacin, ofloxacin, sparfloxacin, trovafloxacin, oxolinic acid, gemifloxacin, perfloxacin, imipenem-cilastatin, meropenem, and aztreonam. In one embodiment, the amount of an antibiotic in a topical composition can be from about 0.01 to 5% by weight of the total composition.

Antiseptic compounds include, but are not limited to, iodine, manuka honey, octenidine dihydrochloride, phenol, polyhexanide, sodium chloride, sodium hypochlorite, calcium hypochlorite, sodium bicarbonate, methyl paraben, benzoyl peroxide and sodium dehydroacetate. In one embodiment, the amount of an antiseptic compound in the topical formulation can be from 0.01 to 5% by weight of the total composition.

Antifungal agents include, but are not limited to, amphotericin B, candicidin, filipin, hamycin, natamycin, nystatin, rimocidin, bifonazole, butoconazole, clotrimazole, econazole, fenticonazole, isoconazole, ketoconazole, luliconazole, miconazole, omoconazole, oxiconazole, sertaconazole, sulconazole, tioconazole, albaconazole, fluconazole, isavuconazole, itraconazole, posaconazole, ravuconazole, terconazole, voriconazole, abafungin, amorolfin, butenafine, naftifine, terbinafine, anidulafungin, caspofungin, micafungin, benzoic acid, ciclopirox, flucytosine, griseofulvin, haloprogin, tolnaftate, undecylenic acid, crystal violet, and balsam of Peru. In one embodiment, the amount of an antifungal agent in the topical formulation can be from 0.01 to 5% by weight of the total composition.

Analgesic agents include, but are not limited to, methyl salicylate, codeine, morphine, methadone, pethidine, buprenorphine, hydromorphine, levorphanol, oxycodone, fentanyl, and a non-steroidal anti-inflammatory drug. The amount of an analgesic agent in the topical formulation can be from about 0.01 to 5% by weight of the total composition.

Anti-viral agents include, but are not limited to, acyclovir, famciclovir, penciclovir, valacyclovir, trifluridine, docosanol, amantadine, rimantadine, oseltamivir, and zanamivir. The amount of an anti-viral agent in the topical formulation can be from about 0.01 to 5% by weight of the total composition.

In some embodiments, the topical composition of the disclosure may further comprise a stabilizer selected from the group consisting of guar gum, xanthan gum cellulose hyaluronic acid, polyvinyl pyrrolidone (PVP), alginate, chondritin sulfate, poly gamma glutamic acid, gelatin, chitosan, corn starch and flour, in an amount from about 0.25 to 2% (w/v)

Formulations may be prepared by conventional procedures known in the pharmaceutical and cosmetic fields. It will be appreciated that the compositions described herein may be varied according to well-known techniques to accommodate differing amounts and types of ingredients. Additionally, the specific ingredients and proportions described herein are for illustrative purposes. Ingredients may be exchanged for suitable equivalents or substitutes, and proportions may be varied, according to the desired properties of the dosage form of interest.

In some embodiments, the products are acne bacteria eliminating and collagen creating accelerants when they come in contact with the skin of a human or animal. The products can help to treat acne bacteria, lessen wrinkles, and rejuvenate the skin, while also providing other good skin hygiene benefits, such as hydrating the skin with a high viscosity (heavy) night cream with a sleep encouraging lavender scent. Cannabinoids have anti-inflammatory attributes, which can also help to further moisturize, shrink, plump and smooth skin where needed. (CBD and CBD/THC) are Natural plant-based compositions comprising's that are useful for treating acne and other skin disorders, while also providing skin rejuvenating properties, such as hydration and wrinkle diminishment (i.e., collagen boosting attributes). A particular embodiment uses as an anti-acne bacterium, hydrating, topical night cream with skin metabolic and collagen boosting attributes. When a therapeutically amount of the composition is placed in contact with an affected area of a skin disorder, the composition can treat a variety of skin disorders, such as, acne, xerosis (or xeroderma), and/or wrinkled skin.

CBD and/or THC inherent characteristics and properties are unexpectedly enhanced by combining it with fatty acid meadow foam seed oil and squalene, which serve as an emollient, penetration enhancer and/or a dispersion agent for the cannabinoid. Efficacy studies on ex vivo human skin show enhanced anti-microbial and skin metabolic enhancing properties for the Example 1 formulations. The anti-microbial and skin metabolic enhancing properties of the inventive compositions make them exceptional skin care products that can promote both skin healing and skin rejuvenation. They may be applied on any part of the skin that needs to be treated for a skin disorder, such as the face, eyes or other parts of the body. Once in contact with the skin, the inventive compositions can provide their beneficial attributes.

A skilled artisan in the field of skin care formulations can utilize the compositions and methods described herein to create a high-quality skin product.

The following Examples are intended to illustrate the above disclosure and should not be construed as to narrow its scope. One skilled in the art will readily recognize that the Examples suggest many other ways in which the disclosure could be practiced. It should be understood that numerous variations and modifications may be made while remaining within the scope of the disclosure.

EXAMPLES

Example 1—Example 1 Formulation with CBD/THC

A skin care composition comprising CBD/THC and meadowfoam seed oil/squalene is formulated to provide Example 1 (CBD/THC) comprising the following ingredients and weight percentages:

Aqua (Purified water) 56.45%, *Limnanthes alba* (Meadowfoam) Seed Oil 15.00%, Neossance Saualane (Squalene) 10%, Cetearyl Alcohol (Plant) 5% and Cetearyl Glucoside and Sorbitan Olivate (Beautyderm K10) 5%, *Olea europaea* (Olive) Oil Unsaponifiables 1%, Ethylhexylglycerin 1%, Caprylhydroxamic Acid and Glyceryl Caprylate and Glycerin 1.2%, Ascorbyl Palmitate and Tocopherol 1.00%, Tetrahydrocannabidiol (89.5%) 0.75%, Cannabidiol (CBD) 0.55%, Sodium Hyaluronate 1.00%, Meadowfoam Delta Lactone 0.50%, Melatonin 0.050%, Glycine Soya (Soybean) Oil and Retinyl Palmitate and Tocopherol Acetate and Ascorbyl Isostearate 0.05%, Xanthan Gum 0.80%, *Lavandula angustifolia* (Lavender) Flower Oil 0.20%.

In addition to the ingredients and weight percentages, the following the general mixing conditions are for making the composition according to the primary functions of the ingredients. For example, in a suitable vessel, add solvent at room temperature, then slowly combine and thickener (add optional anti-oxidant) and mix with LIGHTNIN mixer set at 600-800 rpm. This mixture is mixed for 10 minutes, and heated to 75-80° C. until completely dissolved and homogeneous still mixing at 600-800 rpm. In a separate suitable vessel, premix conditioner, moisturizer, emulsifier and cannabinoid(s) and heat to 80° C. with LIGHTNIN mixer at 500-600R rpm. When both vessels are mixing and have reached between 75-80° C., slowly transfer the premixed conditioner, moisturizer, emulsifier and cannabinoid(s) to the solvent and thickener while maintaining high mixing during and after the transfer. Maintain the 80° C. temperature while mixing at high speed for 5-10 minutes, then start slowing cooling the batch while reducing speed to 400-500R rpm. Cool batch to 55-60° C. and add premixed preservative treatment moisturizer and aroma therapy while mixing at this slower speed and continue to reduce speed as temperature drops. At 50° C., submit a sample to QC for analysis and, if approved, transfer batch at between 40-50° C. for packaging.

Example 2—Example 2 Formulation with CBD (No Added THC)—Anti-Acne Properties

A skin care formulation of Example 1 (CBD/THC) was formulated, except that the ingredient THC was omitted (deionized water was used in its place). This composition was Example 2 (CBD).

Example 2 (CBD) was tested for anti-microbial/anti-acne effectiveness and the results were compared to the effectiveness of a control—a "Base" (ingredients of Example 1 (CB/THC) with no cannabinoids)—and two commercial anti-acne products—Proactiv® Repair (benzoyl peroxide, 2.5%) and Neutrogena® Rapid Clear Acne Eliminating Spot Gel (salicylcic acid, 2.0%). To determine the antimicrobial properties of the four compositions, ex vivo human skin was obtained via post-surgical elective surgery under IRB protocol and prepared as 5 mm explants. *Cutebacterium acnes* (ATCC 6919) was inoculated to the surface of the ex vivo human skin explants for 2 h incubation prior to treatment with each of the four compositions. After 24 h exposures and incubation, *C. acnes* bacterial densities were determined via plating on agar and colony counts (n=3; mean+/−SEM), whereby the log reduction in bacterial counts were calculated for each study. The resultant colony counts are listed in FIG. 1.

Figure 1:
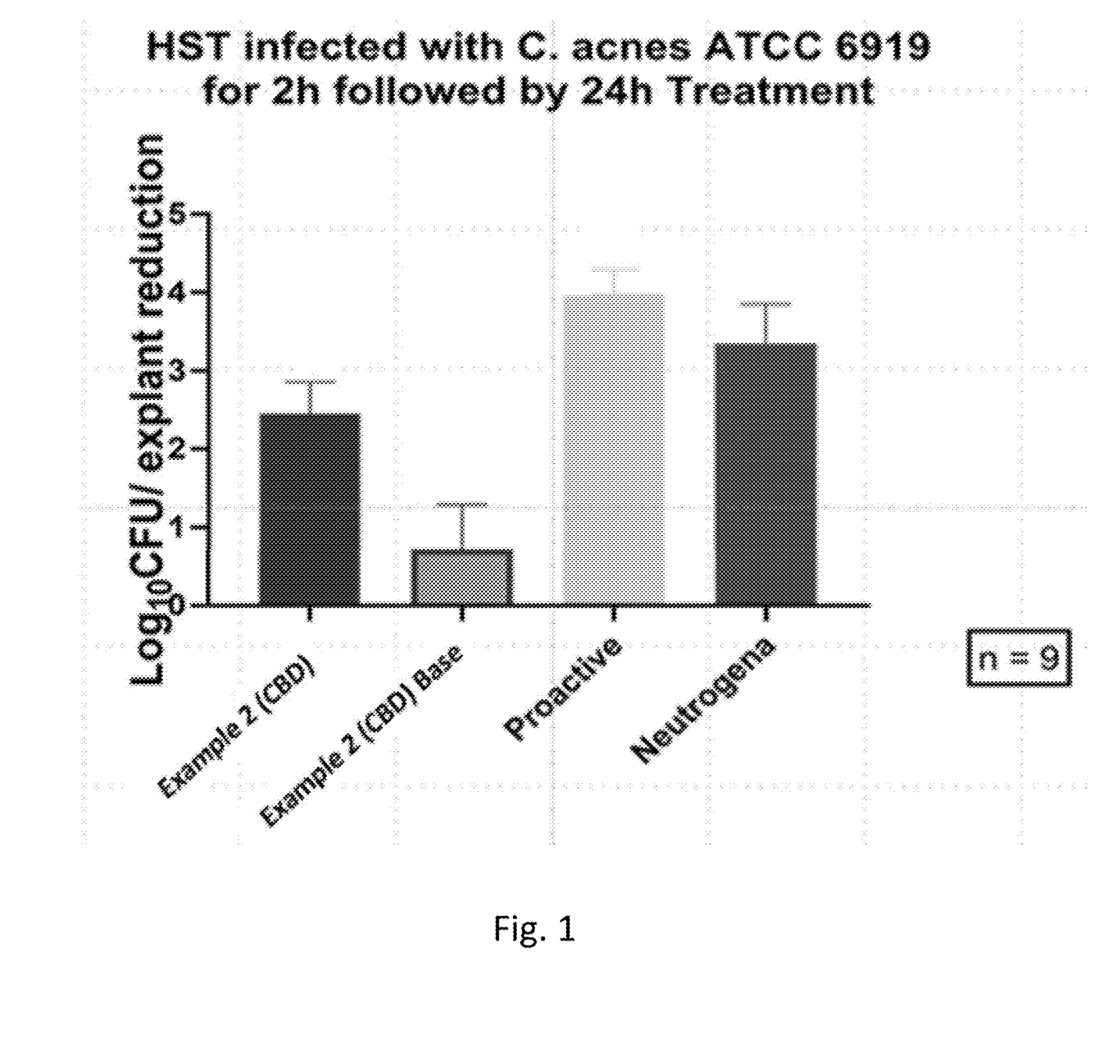
FIG. 1 lists the resultant *C. acnes* colony counts for the samples tested in Experiment 2.

The Example 2 (CBD) composition reduced *C. acnes* growth almost on par with the growth controls provided by the two commercial products, 2.5% benzoyl peroxide (Proactiv®) and 2.0% salicylic acid (Neutrogena®). On the other hand, the Base composition (lacking any cannabinoids) did not significantly reduce *C. acnes* growth. In this example, 0.55% of CBD in the formulation significantly enhanced the anti-acne properties versus the Base composition.

Example 3—Example 2 CBD)—Toxicity and Metabolic Properties

Figure 2:
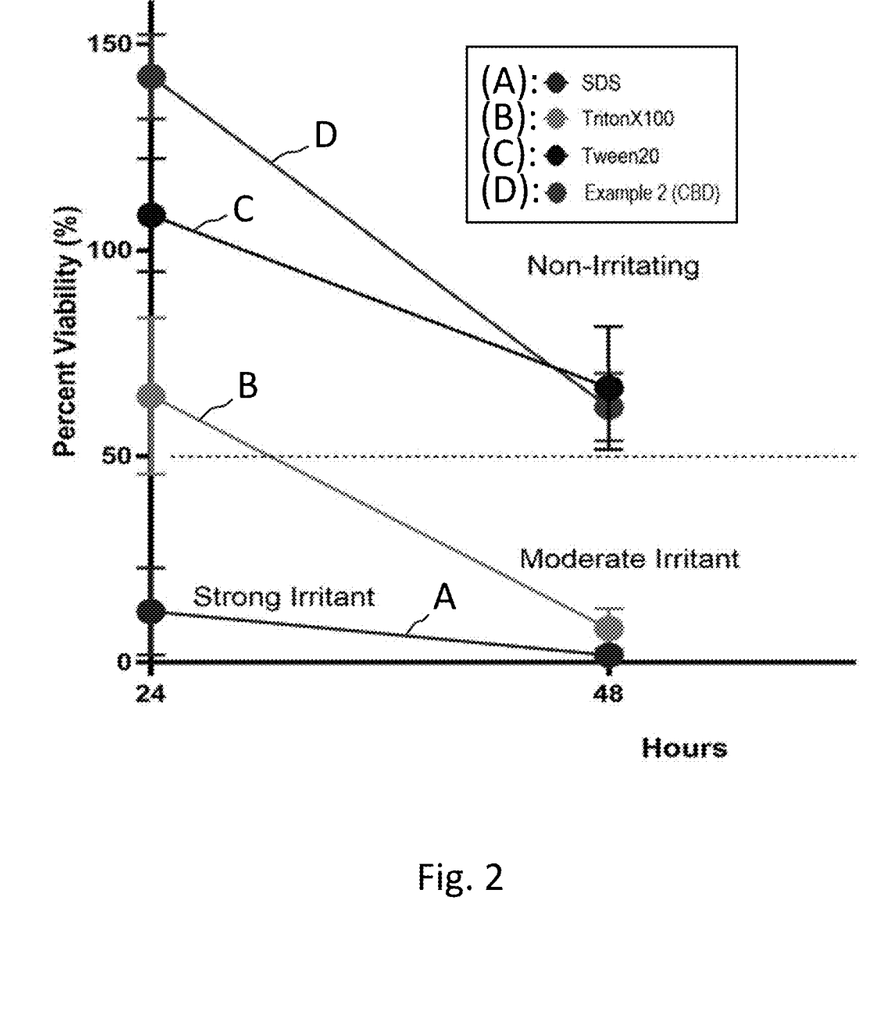
FIG. 2 lists the cell viability results tested in Example 3.

Example 2 (CBD) was also tested to determine its toxicity and metabolic properties in comparison to a control and three commercial cleaning agents (irritants)—"SDS" (sodium dodecyl sulfate), Triton™ X-100, and Tween® 20. Once again, ex vivo human skin was obtained via post-surgical elective surgery under IRB protocol and prepared within 2 hours of surgery as 5 mm explants. The compositions were applied to the surface of the epidermis and incubated for 24 hours and 48 hours at 37° C. At each time point, explants were assessed for viability and metabolic activity via a MTT assay (n=3; mean+/−SEM), a colorimetric assay for assessing cell metabolic activity. After twenty-four hours post-exposure, the Example 2 (CBD) composition exhibited enhanced metabolic activity beyond the metabolic activities of untreated ex vivo human skin explants, which were better than the metabolic activities shown by SDS, Triton® X-100, and Tween® 20. The metabolic activity (viability) of tissues treated with Example (CBD) remained above 50% at 48 hours post treatment compared to the untreated skin control, while those treated with Trition® X-100 and SDS were <10% and are illustrated in FIG. 2 shows the testing results for the samples tested in this example.

The metabolic enhancement properties of Example 2 (CBD), when it comes in contact the skin, can promote skin rejuvenation properties, such as collagen rejuvenation, desquamation (increased epidermal turnover), and product application can accelerate the cell cycle with a faster turnover rate, yielding improvements in skin appearance.

Example 4—Composition A1 Viability Studies (MTT) on Ex Vivo Human Skin

The efficacy of active composition A1 on the viability human skin was assessed using the following compositions and procedures.
Active Composition A1:
  Meadowfoam Seed Oil 5 wt %, Tetrahydrocannabidiol 0.3 wt %, Cannabidiol 0.3 wt %, Base Composition A2 94.4 wt %.
Base Composition A2:
  Aqua, Squalane, Cetearyl Alcohol (Plant), Cetearyl Glucoside, Sorbitan Olive, Niacinamide, Olea europaea (Olive) Fruit Oil, Ethylhexylglycerin, Caprylhydroxamic Acid, Glyceryl Caprylate, Glycerin, Acorbyl Palmitate, Sodium Hyaluronate, Meadowfoam Delta Lactone, Glycine Soya (Soybean) Oil, Retinyl Palmitate, Tocopherol Acetate, Ascorbyl Isostearate, Xanthan Gum, Lavandula angustifolia (Lavender) Flower Oil, Phospholipids, Melatonin.
Ex Vivo Human Skin Preparation
  Trim a section of abdominal skin large enough to cut the appropriate number of 5 mm explants. Place the skin on a dissection tray, create 5 mm explants, trim, and sonicate for 2±0.1 minutes in RPMI. Wash three times in RPMI.
  Set up 6 well transwell cell culture plates with 1.5 mL of RPMI underneath. Transfer tissue explants epidermis side up to the plate (three explants/well).
  Precondition in incubator for 1 h at 37° C., 5% CO2.
Treatment with Composition A1
  Add 10±0.5 µL treatment/explant. Incubate for 24, 48, or 72 h at 37° C., 5% CO2.
  Every 24 hours wash with saline and aspirate out excess. Replace culture media. Reapply treatment.
  Process zero hour explants prior to treatment and incubation.
Sampling
  Gently wash each explant in five successive wells filled with 200 µL of PBS each.
  Transfer 1 mL of supernatant from each well into an Eppendorf tube and store at −20° C.
  Transfer explants to 100 µL of MTT reagent and incubate at 37° C., 5% CO2 for three hours.
  Transfer explants to 100 µL acidified (0.1M HCl) isopropanol. Seal plate with a plate seal and store overnight at 4° C.
  The following morning, read plates at 570 nm and 690 nm and calculate percent viability from the zero hour control.

Figure 3:
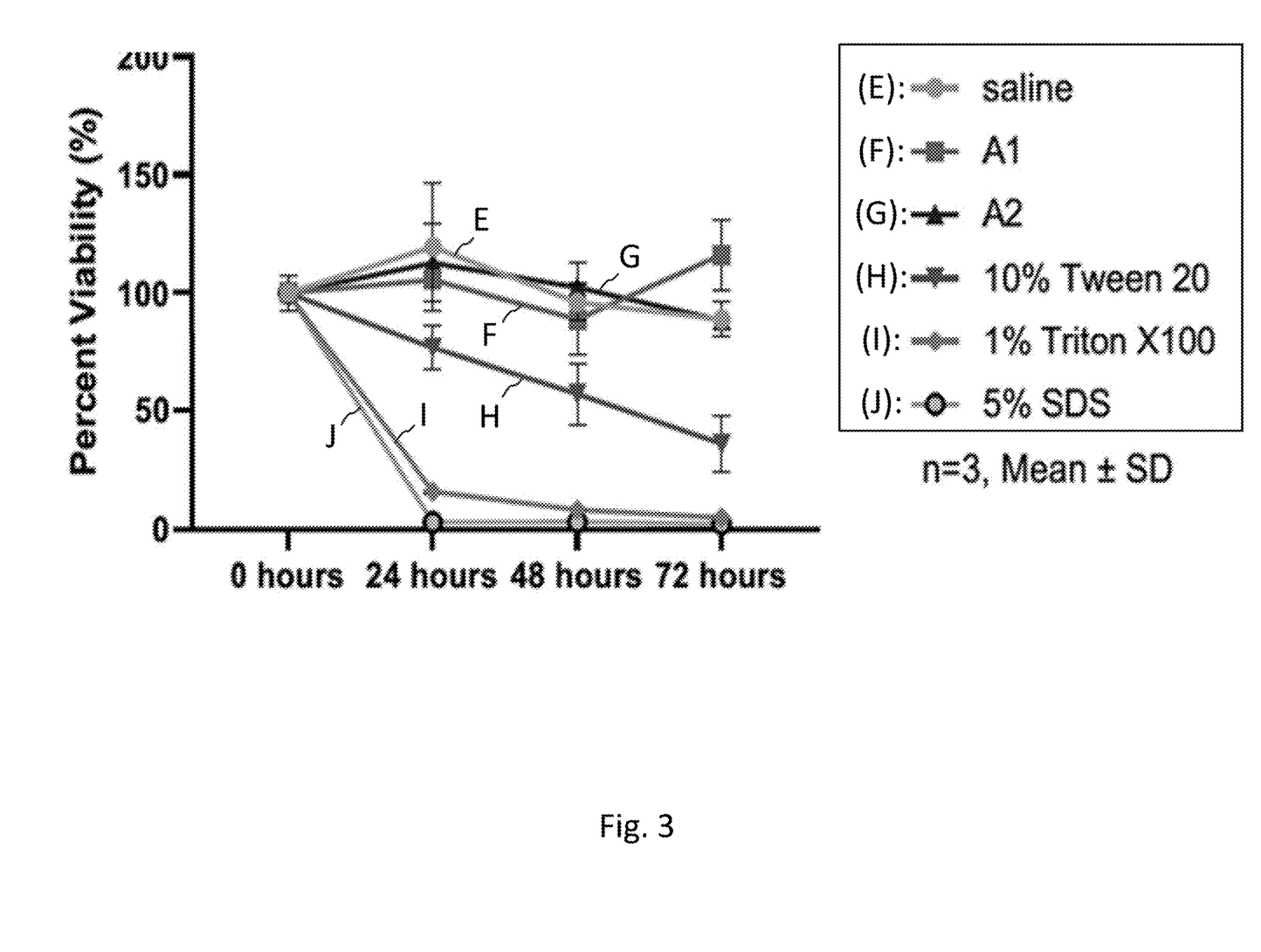
FIGS. 3, 4 and 5 show the metabolic activity data and results for the samples tested in Example 4.
Figure 4:
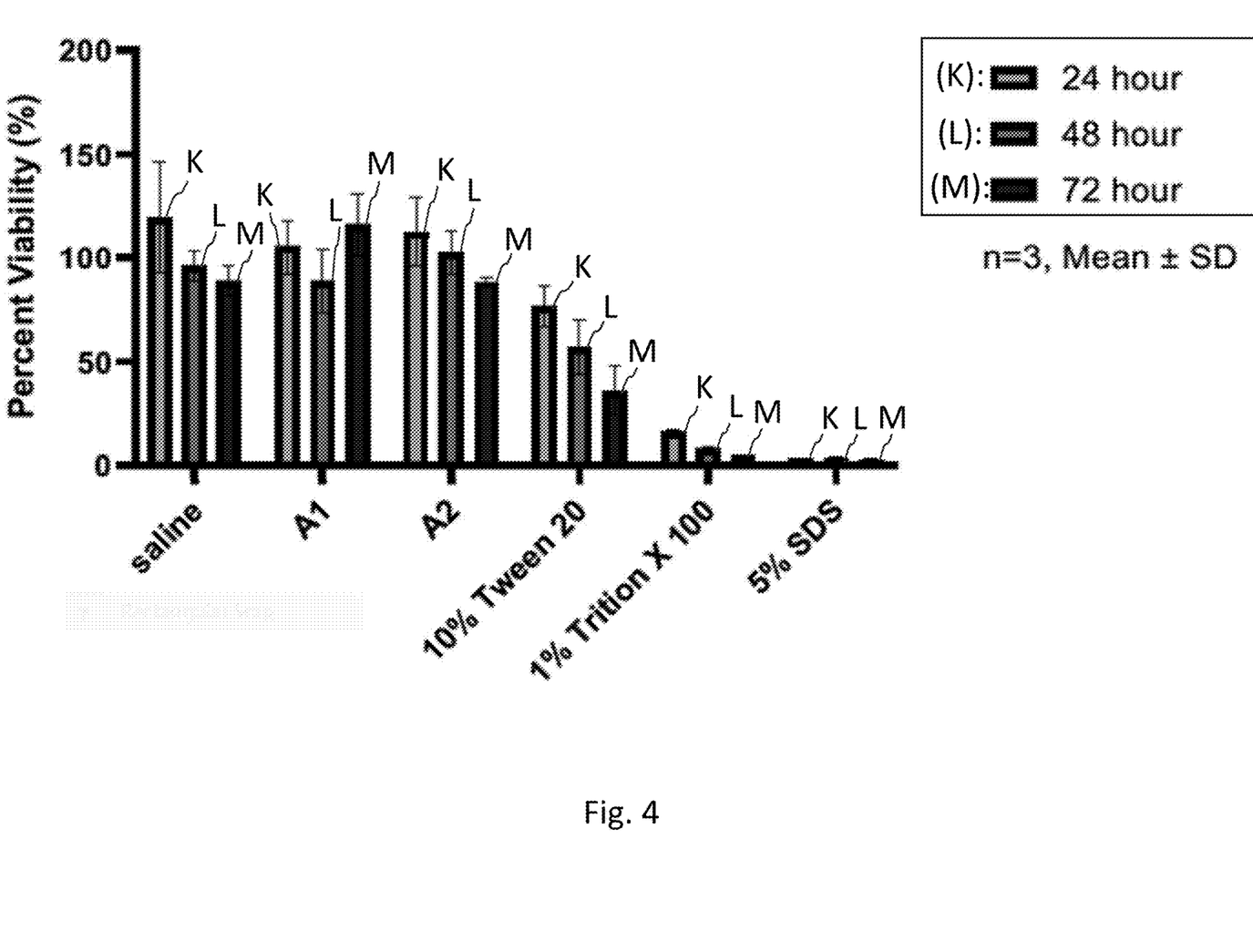
Figure 5:
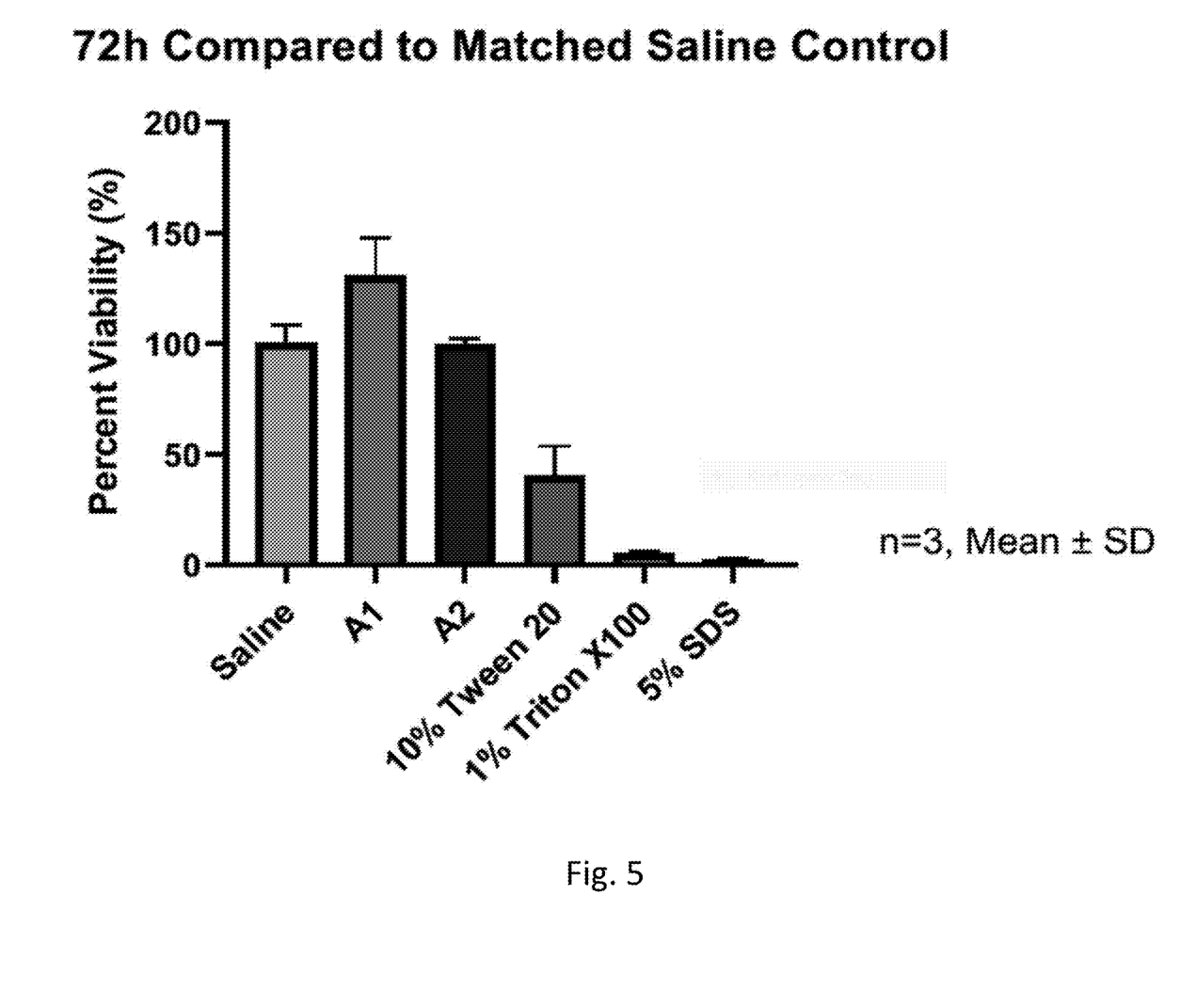

The viability results listed in FIGS. 3, 4 and 5 show that Composition A1 (active) is not irritating and does not reduce viability of human skin and at 72 hours actually was more stimulatory to mitochondrial activity than the saline control.

Example 5—Expression of COL1A1 Using Composition A1

The efficacy of active Composition A1 (same composition as Example 4) to express
COL1A1 in human skin was assessed using the following procedure Ex Vivo Human Skin Preparation
  Place the skin on a dissection tray, create 5 mm explants, trim, and sonicate for 2±0.1 minutes in RPMI. Wash three times in RPMI.
  Precondition in incubator for 1 hour at 37° C., 5% CO2.
  Set up 6 well transwell cell culture plates with 1.5 mL of RPMI underneath. Transfer tissue explants epidermis side up to the plate (5 explants/well).
Treatment with Composition A1
  Add 10±0.5 uL treatment/explant Incubate for 24, 48, or 72 hours at 37° C., 5% CO2.
  Every 24 hours wash with saline and aspirate out excess. Replace culture media.
  Reapply treatment
Sampling
  Gently wash each explant in three successive wells filled with 200 uL of PBS.
  Transfer 1 mL of supernatant to each well into an Eppendorf tube and store at −20° C.
  Transfer explants into individuals cryotubes and snap freeze in liquid nitrogen. o Prechill all tubes, media, etc. and keep everything on ice.
Homogenization
  Place explants individually into 2 mL Triple Pure bead homogenization tubes on ice.
  Add 600 uL of Lysis Buffer.
  Using BeadBug Benchtop Homogenizer, homogenize at max speed for 2 minutes then return to ice bath.
  Centrifuge the homogenized samples individually through the Q1Ashredders at max speed for 2 minutes at 4° C.
  Harvest the flow-through and return immediately to ice bath.
  Extract RNA from homogenate using RNeady Mini kit following kit instructions.
RT-qPCR
  Synthesize cDNA using High Capacity cDNA Reverse Transcription kit
  Perform qPCR using SYBR Green detection chemistry and Beta Actin (housekeeping) and COL1A1 (gene of interest) specific primers[1].
  Analyze data using ΔCt method.

[1] Li J, Ding Y, Li A. Identification of COL1A1 and COL1A2 as candidate prognostic factors in gastric cancer, World J Surg Oncol, 2016 Nov. 29:14(1) 297 doi: 10. 1186/s12957-016-1056-5. PMID: 27894325; PMCID PMCID; PMC5126984.

Figure 6:
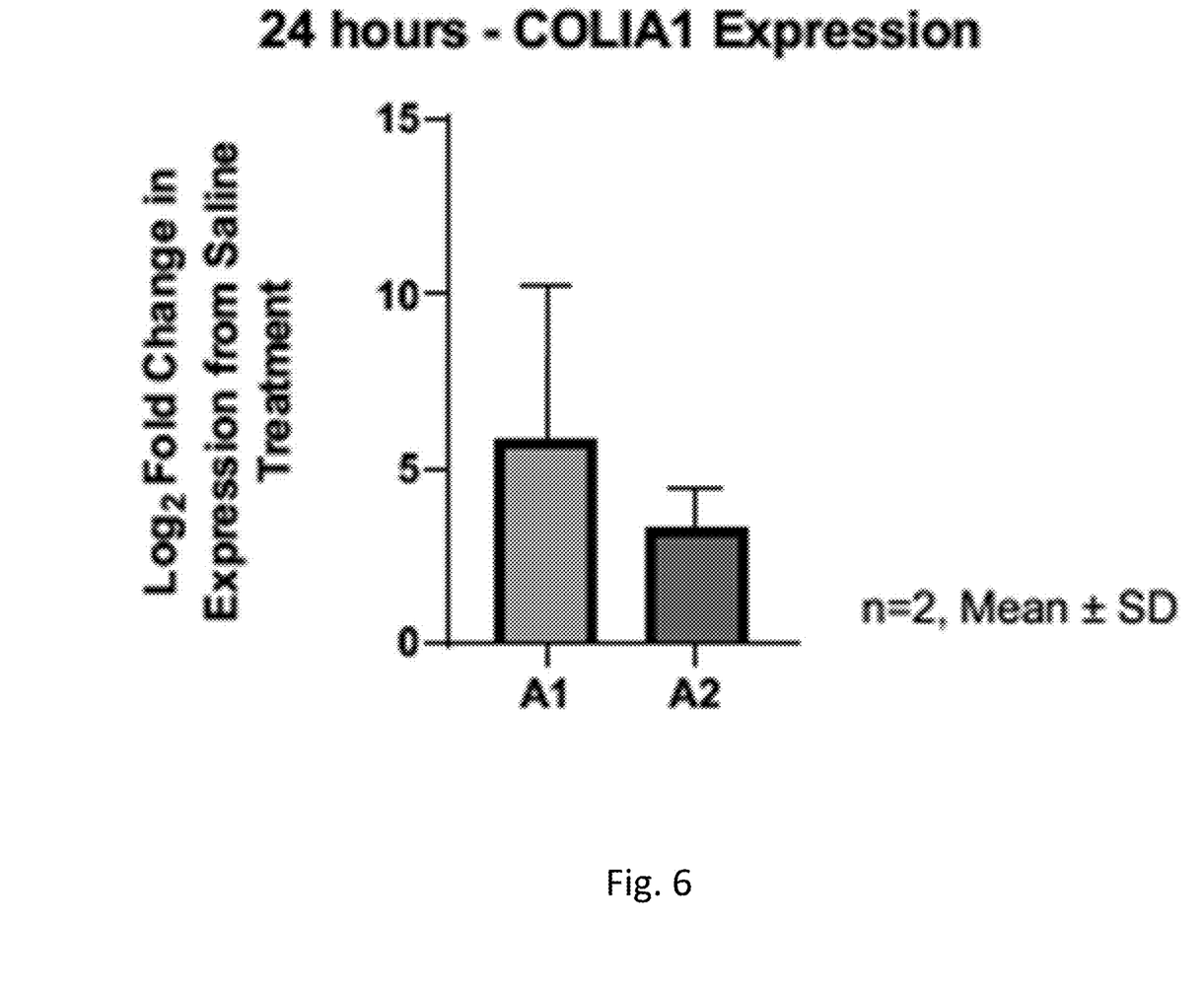
FIGS. 6, 7 and 8 show the gene expression data resulting from the testing done in Example 5
Figure 7:
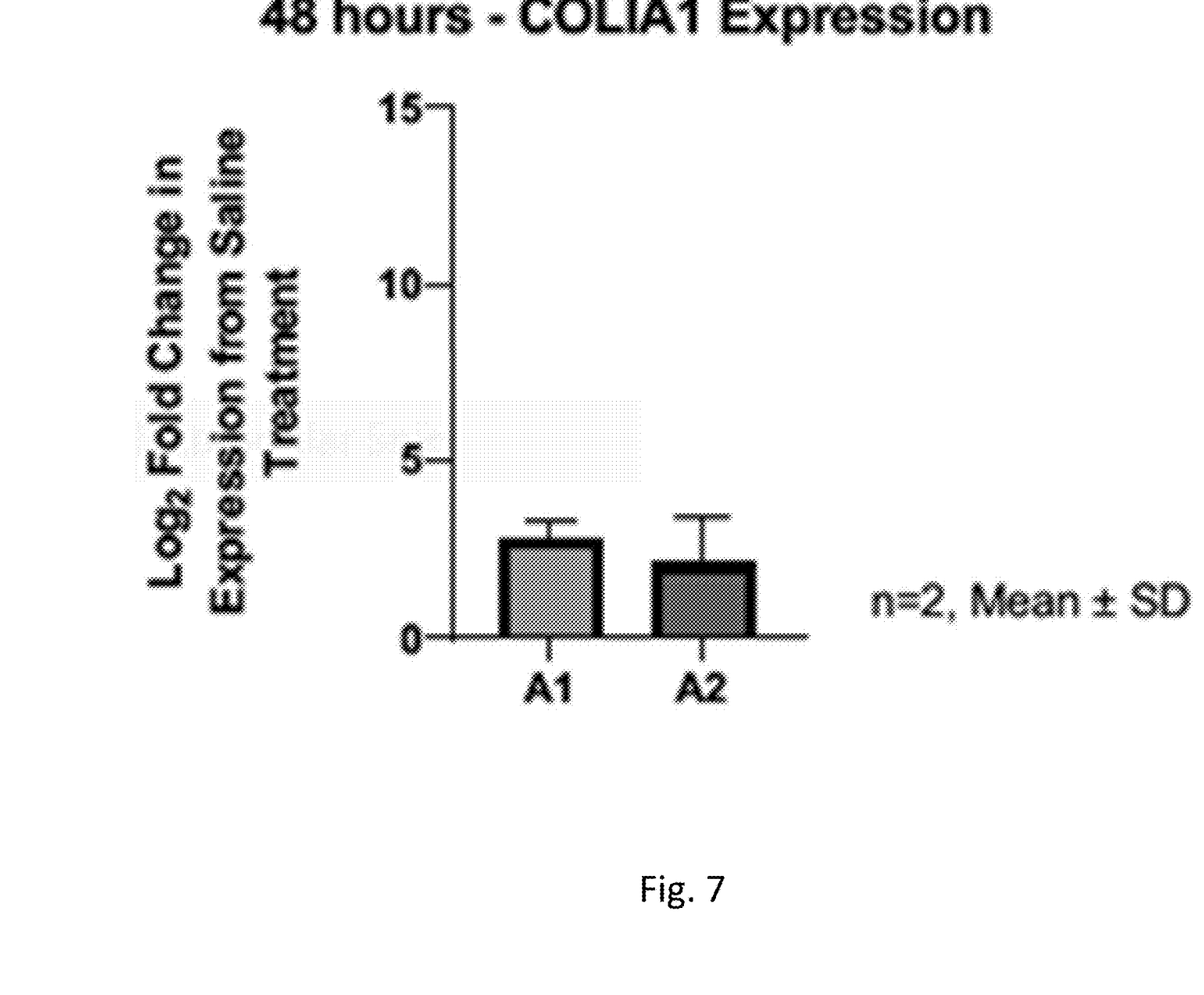
Figure 8:
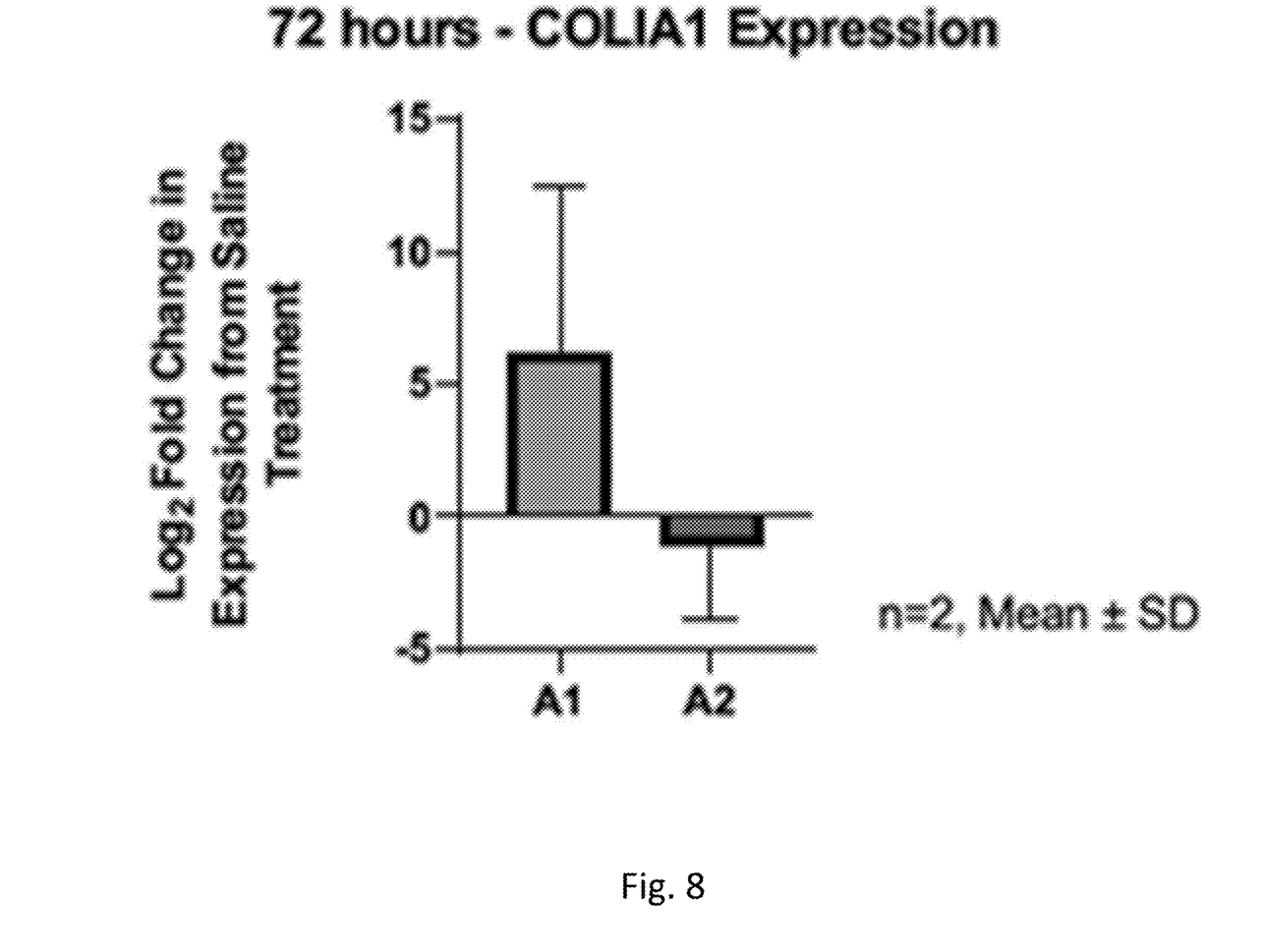

The summary of the resulting data displayed in FIGS. 6, 7 and 8 show that the active composition A1 boosted collagen I gene expression 3 to 6 fold compared to saline controls over 24 to 72 hours.

Example 6—Composition A1 Activity Against *C. acnes* 6919

The efficacy of active Composition A1 (same composition as Example 4) to treat *C. acnes* was assessed by the following procedure.

Figure 9:
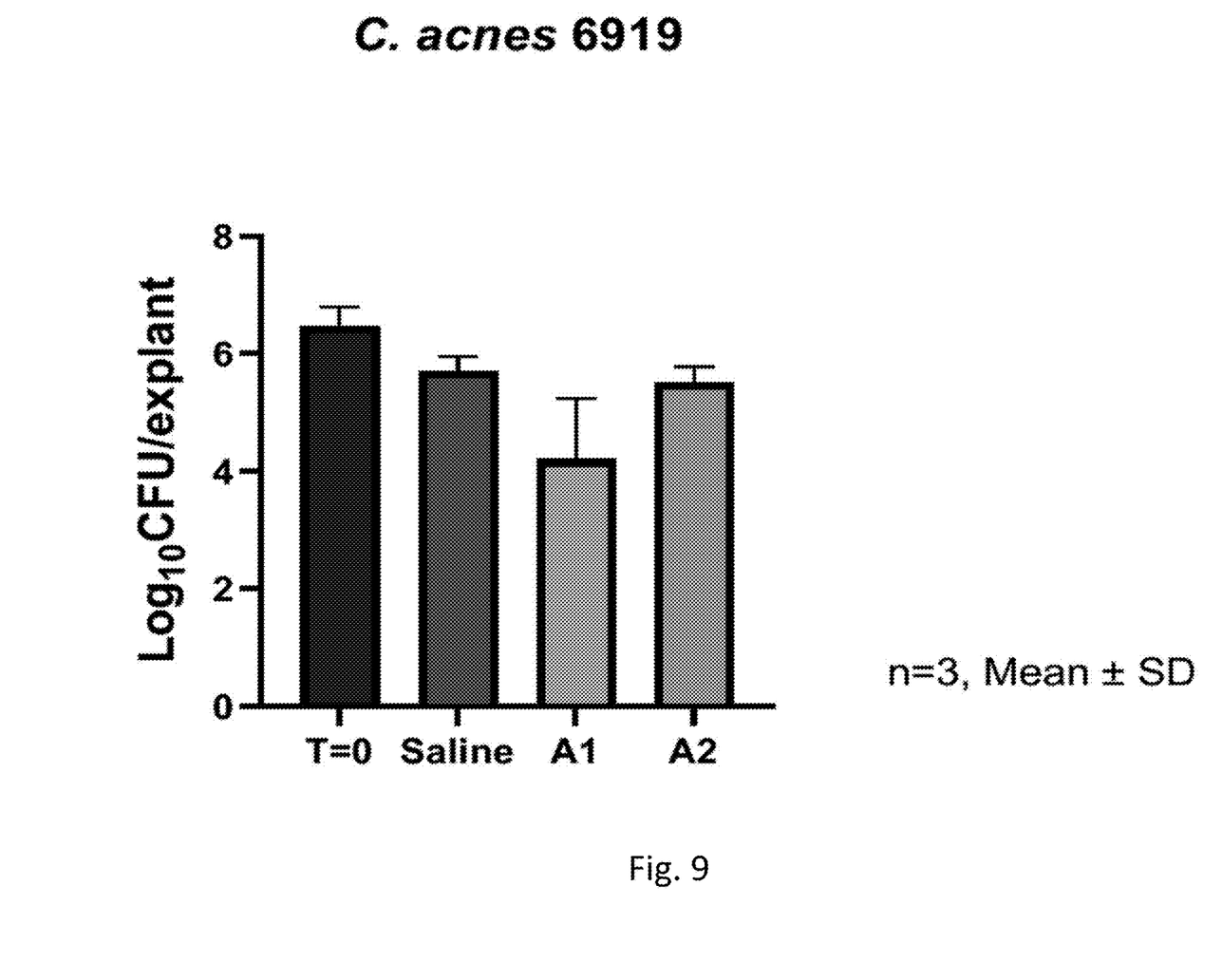
FIG. 9 shows the resultant *C. acnes* colony counts for the samples tested in Experiment 6.

Ex Vivo Human Skin Preparation
  Trim a section of abdominal skin large enough to cut the appropriate number of 5 mm explants.
  Place the skin on a dissection tray, create 5 mm explants, trim, and sonicate for 2±0.1 minutes in RPMI. Wash three times in RPMI 1640.
  Set up 6 well transwell cell culture plates with 2 mL of RPMI 164 underneath. Transfer tissue explants epidermis side up to the plate (3 explants/well).
Infection with *C. acnes* 6919
  Streak *C. acnes* 6919 from freeze within one week of experiment.
  Inoculate 5 m L of TSB with multiple colonies and incubate at 37° C., 220 rpm for 48 hours.
  Pellet bacteria and resuspend in 1 mL of TSB.
  Inoculate explants with 20 uL of culture and incubate for 2 hours.
Treatment
  Collect and plate zero hour control.
  Add 100±2 uL treatment/explant. Incubate anaerobically for 24 h at 37° C.
Sampling
  Transfer explants to 1 mL of neutralizer (2×DE)
  Vortex (30 sec), sonicate (2 min), vortex (30 sec) to liberate bacteria.
  Plate onto blood agar plates and incubate anaerobically for 3 days at 37'C. o Plate neat and 10-2 dilutions with spiral plater.
  Count plates on Protos Plate Counter
  Composition A1 (active) significantly killed the *C. acnes* 6929 when compared with either saline or Base Composition A2 (vehicle control) as shown by the results set out in FIG. 9.

While specific embodiments have been described above with reference to the disclosed embodiments and examples, such embodiments are only illustrative and do not limit the scope of the disclosure. Changes and modifications can be made in accordance with ordinary skill in the art without departing from the disclosure in its broader aspects as defined in the following claims.

All publications, patents, and patent documents are incorporated by reference herein, as though individually incorporated by reference. No limitations inconsistent with this disclosure are to be understood therefrom. The disclosure has been described with reference to various specific and preferred embodiments and techniques. However, it should be understood that many variations and modifications may be made while remaining within the spirit and scope of the disclosure.

What is claimed is:

1. An anti-microbial composition for use on skin comprising the combination of a pharmacologically effective amount of one or more cannabinoids and one or more components comprising about 5.00-20.00% by weight of meadowfoam seed oil and about 4.00-15.00% by weight of hydrogenated squalene in a suitable base.

2. The composition of claim 1, where the cannabinoid and the one or more components each comprise a naturally derived product.

3. The composition of claim 1, where the cannabinoid comprises CBD, THC, or CBD and THC.

4. The composition of claim 3, where the cannabinoid comprises CBD.

5. The composition of claim 3, where the CBD comprises about 0.25-1.10% by weight of the total composition.

6. The composition of claim 3, where the cannabinoid further comprises THC.

7. The composition of claim 3, where the cannabinoid comprises about 0.25-1.10% by weight of CBD and about 0.25-1.50% by weight of THC the total composition.

8. The composition of claim 1 further comprising one or more of the following ingredients: a solvent, a thickener, an anti-oxidant, a conditioner, a moisturizer, an emulsifier, a nutrient, an aroma or fragrance, a preservative, a stabilizer, or a combination thereof.

9. The composition of claim 1, wherein the composition comprises an ointment, a cream, an emulsion, a lotion, a paste, an unguent, a gel or a sunscreen.

10. The composition of claim 1, wherein the composition comprises a cream.

11. A method to treat a skin disorder in a subject comprising applying the composition of claim 1 to an affected area of the skin disorder.

12. The method of claim 11, wherein the skin disorder comprises acne.

13. The method of claim 12, wherein the skin disorder further comprises xerosis.

14. The method of claim 12, where the skin disorder further comprises wrinkled skin.

* * * * *